United States Patent [19]
Ferguson

[11] Patent Number: 5,943,115
[45] Date of Patent: Aug. 24, 1999

[54] SERVO TRACKING SYSTEM UTILIZING PHASE-SENSITIVE DETECTION OF REFLECTANCE VARIATIONS

[75] Inventor: R. Daniel Ferguson, Melrose, Mass.

[73] Assignee: Physical Sciences, Inc., Andover, Mass.

[21] Appl. No.: 09/063,519

[22] Filed: Apr. 21, 1998

Related U.S. Application Data

[63] Continuation of application No. 08/636,668, Apr. 23, 1996, Pat. No. 5,767,941.

[51] Int. Cl.⁶ .................................................... A61B 3/14
[52] U.S. Cl. ............................................................ 351/209
[58] Field of Search ................................... 251/200, 205, 251/206, 209, 210, 221; 372/38

[56] References Cited

U.S. PATENT DOCUMENTS

| | | | |
|---|---|---|---|
| 4,264,152 | 4/1981 | Crane | 351/1 |
| 4,443,075 | 4/1984 | Crane | 351/209 |
| 4,561,436 | 12/1985 | Munnerlyn | 128/303.1 |
| 4,764,005 | 8/1988 | Webb et al. | 351/205 |
| 4,765,730 | 8/1988 | Webb | 351/205 |
| 4,781,453 | 11/1988 | Kobayashi | 351/205 |
| 4,856,891 | 8/1989 | Pflibsen et al. | 351/210 |
| 4,881,808 | 11/1989 | Bille et al. | 351/221 |
| 4,924,507 | 5/1990 | Chao et al. | 382/31 |
| 4,931,053 | 6/1990 | L'Esperance, Jr. | 606/2 |
| 4,964,717 | 10/1990 | Koester | 351/219 |
| 5,029,220 | 7/1991 | Juday | 382/6 |
| 5,094,523 | 3/1992 | Reznichenko et al. | 351/221 |
| 5,098,426 | 3/1992 | Sklar et al. | 606/5 |
| 5,106,184 | 4/1992 | Milbocker | 351/221 |
| 5,122,135 | 6/1992 | Durr et al. | 606/4 |
| 5,129,400 | 7/1992 | Makino et al. | 128/666 |
| 5,243,368 | 9/1993 | Ito et al. | 351/221 |
| 5,252,999 | 10/1993 | Sukigara et al. | 351/221 |
| 5,347,329 | 9/1994 | Ota | 351/221 |
| 5,353,073 | 10/1994 | Kobayashi | 351/221 |
| 5,360,010 | 11/1994 | Applegate | 128/745 |
| 5,360,424 | 11/1994 | Klopotek | 606/4 |
| 5,425,729 | 6/1995 | Ishida et al. | 606/13 |
| 5,430,509 | 7/1995 | Kobayashi | 351/221 |
| 5,480,396 | 1/1996 | Simon et al. | 606/4 |
| 5,778,016 | 7/1998 | Sucha et al. | 372/38 |

FOREIGN PATENT DOCUMENTS

| | | | |
|---|---|---|---|
| 0770370 | 5/1997 | European Pat. Off. | A61F 9/00 |
| WO90/09141 | 8/1990 | WIPO . | |
| WO93/08877 | 5/1993 | WIPO | A61N 5/02 |
| WO95/28989 | 11/1995 | WIPO | A61N 5/06 |

OTHER PUBLICATIONS

International Search Report for corresponding PCT application No. PCT/US97/06581 dated Sep. 3, 1997.

*Primary Examiner*—George Manuel
*Attorney, Agent, or Firm*—Testa, Hurwitz & Thibeault, LLP

[57] ABSTRACT

Apparatus and methods for tracking a feature on a target surface and continually providing analog corrections to tracking mirrors in real time by utilizing a low-power incoherent tracking beam to detect the movements of a reference feature on the target and confocal reflectometry to monitor the reflection from the tracking beam's current position are described. The apparatus includes a dithering device for dithering the tracking beam in a first and a second direction with an oscillatory motion, a tracking device for controlling the position of a therapeutic beam relative to a target and for controlling the position of the tracking beam relative to a reference feature, a reflectometer for providing an output signal with a phase corresponding to a phase of the reflected tracking beam, and a signal processor for comparing the phase of the reflectometer output signal to the phases of the oscillatory motion and for controlling the tracking device so that the therapeutic beam to tracks relative to the reference feature.

14 Claims, 4 Drawing Sheets

SERVO TRACKING SYSTEM UTILIZING PHASE-SENSITIVE DETECTION OF REFLECTANCE VARIATIONS

RELATED APPLICATION

This is a continuation of application Ser. No. 08/636,668, filed Apr. 23, 1996 now U.S. Pat. No. 5,767,941.

GOVERNMENT SUPPORT

This invention was made with government support under contract number 1214 awarded by the National Institutes of Health. The U.S. government has certain rights in the invention.

FIELD OF THE INVENTION

The invention relates generally to the field of target tracking. In particular, the invention relates to apparatus and methods for reflectance-based servo tracking for image stabilization and precision target tracking.

BACKGROUND OF THE INVENTION

Active servo tracking systems are used in numerous military, industrial, and medical applications. In operation, active servo tracking systems utilize information about a target's motion to correct the physical position of an object to be stabilized in a target frame of reference. The information about the target's motion may be obtained by numerous techniques such as direct position measurements, position correlation, and velocity sensing.

Direct position measurement techniques for obtaining information about a target's motion typically utilize position sensitive detectors, such as quadrant detectors, to detect a "hot spot" associated with the target. Position correlation techniques for obtaining information about a target's motion compare previously stored images of the target to the current image at predetermined time intervals. The resulting image overlap or correlation function is utilized to determine the target displacement.

Velocity sensing techniques for obtaining information about a target's motion typically utilize a signal proportional to the rate of displacement in the frequency domain. The signal is then integrated to give target position information. There are numerous velocity sensing techniques known in the art such as coherent laser-based Doppler and speckle methods.

U.S. Pat. No. 4,856,891 describes an eye fundus tracking system that utilizes active servo tracking and correlation. The system includes a laser source that projects a tracking strip of coherent light on the fundus and optics for producing an image of reflected light from the tracking strip onto a detecting element. The system also includes a means for scanning the intensity profile of the image strip and electronics for analyzing the scanned intensity profile and for providing correction signals which direct the optical path of both the tracking laser beam and a diagnostic laser beam to a fixed position on the fundus. The system, however, is relatively complex to implement.

Numerous applications, such as ophthalmologic and other micro-surgical procedures, require high-speed positioning with accuracy in the cellular dimension range. In addition, it is desirable for such tracking systems to utilize low-power incoherent tracking beams.

SUMMARY OF THE INVENTION

It is a principal object of this invention to provide apparatus and methods for tracking a feature on a target surface and continually providing analog corrections to tracking mirrors in real time by utilizing a low-power incoherent tracking beam to detect the movements of a reference feature on the target and confocal reflectometry to monitor the reflection from the tracking beam's current position. It is another object of this invention to utilize small, periodic, transverse oscillations in the tracking beam and phase sensitive detection of the reflectance variations to generate error signals which are utilized to compensate the target displacement.

It is another object of this invention to provide independent steering of a tracking beam and a therapeutic beam by a balanced "scan and de-scan" technique. It is another object of this invention to provide a high-speed fundus tracking system that utilizes confocal reflectometry for retinal photocoagulation.

Accordingly, the present invention features a tracking system for tracking a reference feature on a target surface. The tracking system includes a dithering device positioned in an optical path of a tracking beam. The tracking beam may be formed from a light emitting diode or from numerous other low-power coherent or incoherent light sources.

The dithering device dithers the tracking beam in a first and a second direction with an oscillatory motion having a first and a second phase, respectively. The first and second phases of oscillatory motion may be orthogonal to each other. The dithering device may comprise a pair of orthogonally mounted galvanometers operatively connected to reflectors.

The tracking system also includes a tracking device for controlling the position of a therapeutic beam relative to a target and for controlling the position of the tracking beam relative to a reference feature. The reference feature may be associated with an eye or may be a retro-reflecting material. The tracking device includes a first input for accepting a first direction control signal and a second input for accepting a second direction control signal. The first and second direction control signals cause the tracking device to move the therapeutic beam in the first and second directions, respectively. The tracking velocity of the tracking device may be proportional to the product of a dither frequency of the dithering device and a spatial dimension of the reference feature.

The tracking system also includes a reflectometer positioned in an optical path of a reflected tracking beam. The reflectometer provides an output signal with a phase corresponding to the phase of the reflected tracking beam. The reflectometer may be a confocal reflectometer.

The tracking system also includes a signal processor for comparing the phase of the reflectometer output signal to the phases of the oscillatory motion in the first and second directions. The signal processor generates the first and second direction control signals which are coupled to the first and second inputs of the tracking device, respectively. The first and second direction control signals cause the therapeutic beam to track relative to the reference feature.

The present invention also features an eye tracking system for tracking a reference feature associated with an eye. The eye tracking system includes a first pair of reflectors. The first reflector is positioned in an optical path of an incident and reflected tracking beam. The second reflector may be a beamsplitter that passes a coagulating beam in transmission and reflects the tracking beam in reflection. The first pair of reflectors controls the position of the tracking beam. The tracking beam may be formed from a light emitting diode or from numerous other low-power incoherent light sources.

The eye tracking system also includes a pair of dither drivers operatively connected to the first pair of reflectors. The dither drivers dither the first reflector in a first direction and the second reflector in a second direction with an oscillatory motion having a first and a second phase, respectively. The first and second phases may be orthogonal. The pair of dither drivers may be orthogonally mounted galvanometers operatively connected to the first pair of reflectors.

The eye tracking system also includes a second pair of reflectors for positioning the tracking beam onto a reference feature in an eye and for positioning the coagulating beam onto a target in the eye. The eye tracking system also includes a pair of tracking drivers for controlling the position of the second pair of reflectors. The pair of tracking drivers is operatively connected to the second pair of reflectors and comprises a first input for accepting a first direction control signal and a second input for accepting a second direction control signal. The first and second direction control signals cause the pair of tracking drivers to move the second pair of reflectors in the first and the second direction, respectively. A tracking velocity of the pair of tracking drivers is proportional to the product of a dither frequency of the pair of dither drivers and a spatial dimension of a reference feature.

The eye tracking system also includes a reflectometer positioned in the optical path of the reflected tracking beam. The reflectometer, which may be a confocal reflectometer, provides an output signal with a phase corresponding to a phase of the reflected tracking beam.

The eye tracking system also includes a signal processor for comparing the phase of the reflectometer output signal to the phases of the oscillatory motion in the first and second directions. The signal processor generates the first and the second direction control signals which are coupled to the first and second inputs of the tracking driver, respectively. The first and second direction control signals cause the coagulating beam to track relative to the reference feature.

The eye tracking system may include a shutter for blanking the coagulating beam so that a surgeon can precisely control when the coagulating beam is delivered to the target. The eye tracking system may also include an offset signal generator operatively coupled to the dither driver and to the tracking driver for displacing the coagulating beam with respect to the tracking beam a predetermined distance. When a "scan" signal is input to the tracking driver to reposition the therapeutic beam, an offsetting "de-scan" signal is input to the dither driver. Such an offset signal generator will significantly increase the speed at which the coagulating beam can be translated from one target to another target.

The present invention also features a method of tracking that includes directing a tracking beam to a reference feature. The tracking beam is dithered in a first and a second direction with an oscillatory motion having a first and a second phase, respectively. A reflector is positioned in an optical path of a therapeutic beam. The reflector may also be positioned in an optical path of the tracking beam.

The phase of a reflected tracking beam reflected from the reference feature is measured. The phase of the reflected tracking beam is compared to the first and the second phase of the oscillatory motion. The method also includes repositioning the reflector a distance related to the comparison of the phase of the reflected tracking beam and the first and the second phases of the oscillatory motion where the distance causes the therapeutic beam to track a displacement of the reference feature. In addition, the method may include displacing the therapeutic beam relative to the tracking beam a predetermined distance. The displacement will increase the speed at which the coagulating beam can be translated from one target to another target.

BRIEF DESCRIPTION OF THE DRAWINGS

This invention is described with particularity in the appended claims. The above and further advantages of this invention may be better understood by referring to the following description taken in conjunction with the accompanying drawings, in which:

DETAILED DESCRIPTION

Figure 1:
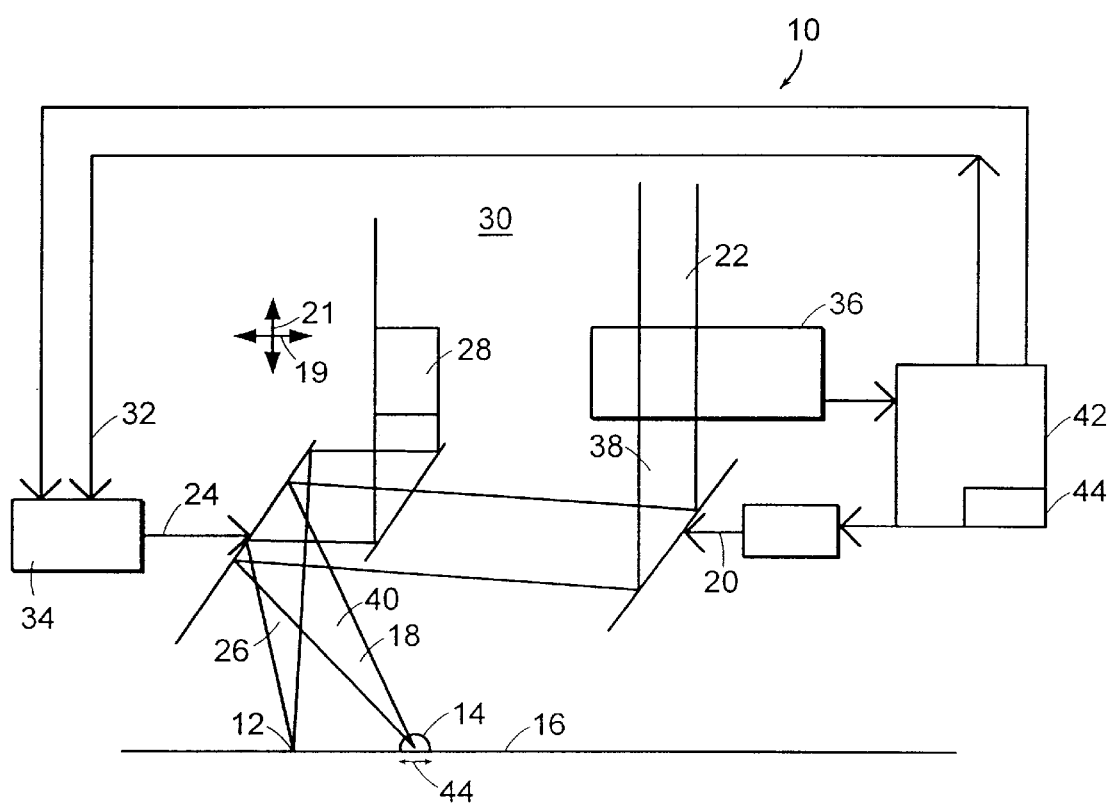
FIG. 1 is a schematic diagram of a tracking system which embodies the invention.

FIG. 1 is a schematic diagram of a tracking system 10 which embodies the invention. The tracking system 10 tracks a target 12 relative to a reference feature 14. The reflectivity of the reference feature 14 is different from the reflectivity of an adjacent background area 16 at the wavelength of a tracking beam 18. The reference feature 14 may be any approximately axisymmetric feature of appropriate size and reflectivity contrast.

The reference feature 14 may be associated with an eye or may be a retro-reflecting material. The reference feature 14 may be photocoagulation eye lesions which are useful for retinal laser surgical application. Photocoagulation lesions are commonly used for marking a physical reference position on the retina. However, many retinal features have a high enough reflectivity contrast with the background area 16 to be suitable as reference features.

The tracking beam 18 locks onto the reference feature 14 by inducing small, periodic, transverse oscillations or dithers in the tracking beam. The tracking beam 18 may be any low-power light beam that detects movement of the reference feature 14. The tracking beam 18 may be formed from a light emitting diode or from numerous other low-power incoherent light sources. Typically, the reference feature 14 is locked onto by the tracking beam in two dimensions with a circular dither.

The tracking system 10 includes a dithering device 20 positioned in an optical path 22 of the tracking beam 18. The dithering device 20 may comprise a pair of orthogonally mounted galvanometers scanner-driven mirrors (not shown). Galvanometers with low armature inertia can be used to achieve a high-speed tracking response.

The dithering device 20 dithers the tracking beam 18 in a first 19 and a second direction 21 with an oscillatory motion having a dither frequency with a first and a second phase, respectively. The dithering device 20 produces a circular dither at the reference feature 12 when the oscillatory motions, in the first and second direction, have identical amplitudes and have a phase difference of 90 degrees.

The tracking system 10 also includes a tracking device 24 for controlling the position of a therapeutic beam 26 relative to the target 12 and for controlling the position of the tracking beam 18 relative to the reference feature 14. The therapeutic beam 26 is typically a high-power coagulating beam. A blanking element 28 may be positioned in an optical path 30 of the therapeutic beam 26 for controlling when the therapeutic beam 26 is delivered to the target 12.

The tracking device 24 includes a first input 32 for accepting a first direction control signal, and a second input 34 for accepting a second direction control signal. The first and second direction control signals cause the tracking device 24 to move the therapeutic beam 26 in the first and the second direction, respectively. The tracking velocity of the tracking device 24 may be proportional to the product of the dither frequency and a spatial dimension of the reference feature 12.

The tracking system 10 also includes a reflectometer 36 positioned in an optical path 38 of a reflected tracking beam 40. The reflectometer 36 provides an output signal with a phase corresponding to a phase of the reflected tracking beam 40. The reflectometer 36 may be a confocal reflectometer. When the tracking beam 18 traverses a region of changing reflectance (not shown), a corresponding variation in the output signal of the reflectometer 36 occurs. The reflectometer output signal varies synchronously (when appropriately corrected for phase shifts) with the oscillatory motion caused by the dither driver 20.

The tracking system 10 also includes a signal processor 42 for comparing the phase of the reflectometer output signal to the phases of the oscillatory motion in the first and second directions. The signal processor 42 generates the first and the second direction control signals which are coupled to the first 32 and second input 34 of the tracking device 24, respectively. The first and second direction control signals cause the therapeutic beam 26 to track relative to the reference feature 14. The maximum tracking velocity of such a tracking system is determined by the dither frequency and a diameter 44 of the reference feature 14.

The signal processor 42 may include an offset signal generator 44, that is operatively coupled to the dithering device 20 and to the tracking device 24 via the signal processor 42, for displacing the therapeutic beam 26 with respect to the tracking beam 18 a predetermined distance. Such an offset signal generator 44 can be utilized to increase the speed at which the therapeutic beam 26 is translated from one target to another target. By providing equal and opposite voltages to the dithering device 20 and to the tracking device 24, the therapeutic beam 26 can be translated relative to the tracking beam 18 much more quickly than the maximum tracking velocity.

Figure 2:
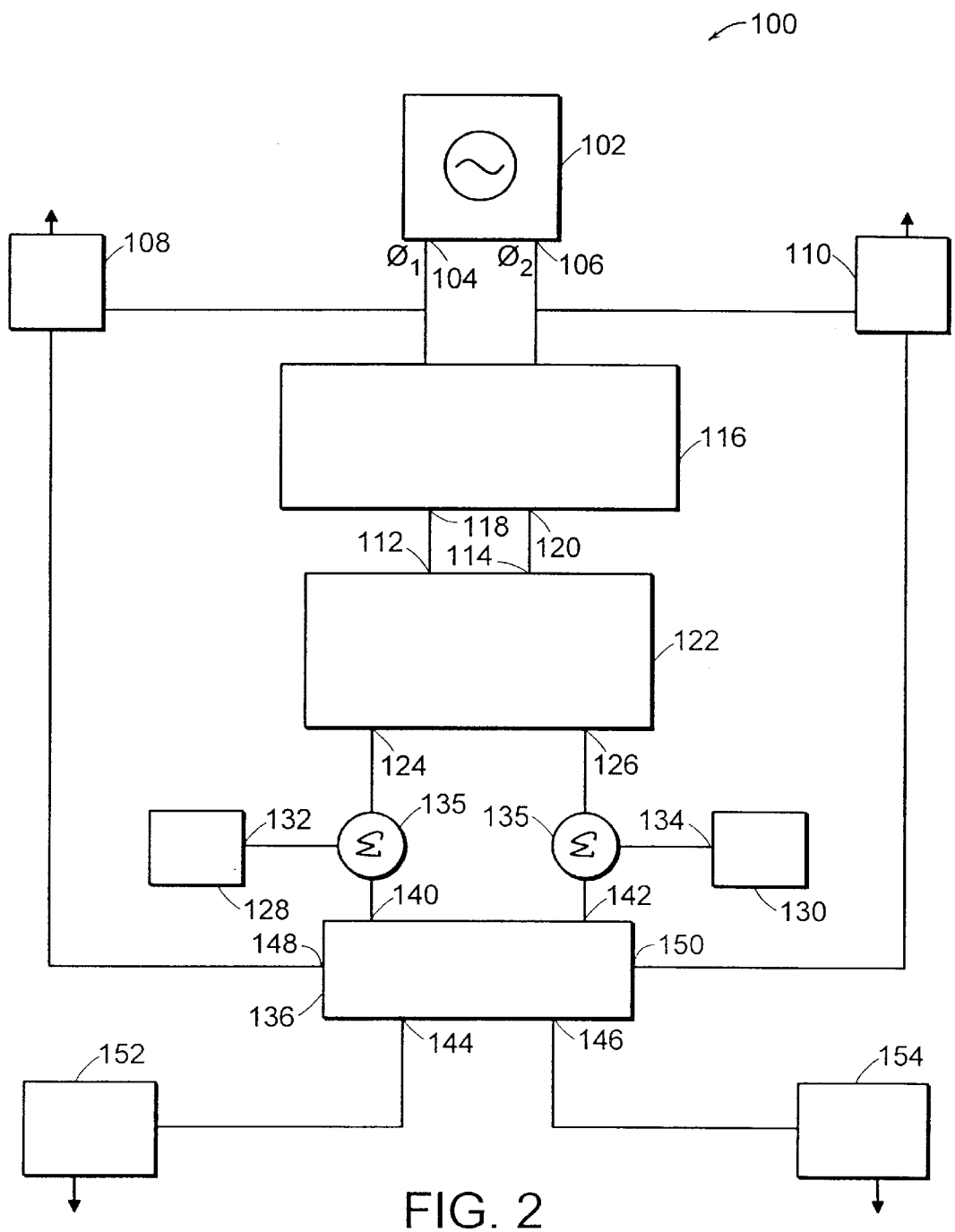
FIG. 2 is a functional block diagram of a signal processor utilized in the tracking systems which embody the invention.

FIG. 2 is a functional block diagram 100 of the signal processor 42 (FIG. 1) utilized in the tracking systems which embody the invention. The signal processor 42 includes an oscillator 102 having a first 104 and a second output 106. The first 104 and the second output 106 have a first and a second phase, respectively, which differs by 90 degrees. The first 104 and the second output 106 of the oscillator 102 are coupled to a first 108 and a second dither driver 110 of the dithering device 20 (FIG. 1) and cause the transverse dithers in the first and the second direction with equal amplitude and a phase difference of 90 degrees.

The signal processor 100 also includes a phase-sensitive detector 116 that may comprise a combination of a narrow-band amplifier circuit (not shown), such as an analog multiplication or mixing circuit, and a low-pass filter (not shown). The phase-sensitive detector 116 electronically compares the phase of the reflectometer signal to the phases of the oscillatory motion in the first and second directions and generates a first and second phase comparison signal at a first 118 and second output 120, respectively.

The first and second phase comparison signals comprise DC offset voltages which are proportional to the amplitude of the components of the reflectometer signal which are in phase with the dither signals. These DC offset voltages are vector correction or error voltages that are proportional to the displacement from equilibrium per dither cycle.

The signal processor 100 also includes an integrator 122 having a first 112 and a second input 114 connected to the first 118 and second output 120 of the phase-sensitive detector 116. The integrator 122 produces a first and a second integrated signal of the first and the second phase comparison signal, respectively. In addition, the signal processor 100 may include a first 128 and a second trim voltage power supply 130 which has a first 132 and a second trim voltage output 134. The first 132 and the second trim voltage output 134 are summed at a node 135 with the first 124 and the second output 126 of the integrator 122. The first 128 and second trim voltage supply 130 may be used to compensate for voltage drifts in the electronics of the signal processor 100.

The signal processor 100 also includes an offset signal generator 136 that accepts the summed outputs of the trim voltage supplies 128, 130 and the integrator 122 at a first 140 and a second 142 input. The offset signal generator 136 produces a first and a second directional control signal at a first 144 and a second output 146, respectively. The first and a second directional control signal are connected to a first 152 and a second tracking driver 154 of the tracking device 24 (FIG. 1).

The offset signal generator 136 also produces a first and a second offset signal at a third 148 and a fourth output 150. The third 148 and the fourth output 150 of the offset signal generator are connected to the first 108 and the second dither driver 110 of the dithering device 20 (FIG. 1). The offset signal generator 136 may be utilized to displace the therapeutic beam 26 (FIG. 1) with respect to the tracking beam 18 (FIG. 1) a predetermined distance. The offset signal generator 136 can greatly increase the speed at which the therapeutic beam 26 is translated from one target to another target. By providing equal and opposite voltages to the dither and the tracking drivers, the therapeutic beam can be translated relative to the tracking beam 18 much more quickly than the maximum tracking velocity.

Figure 3:
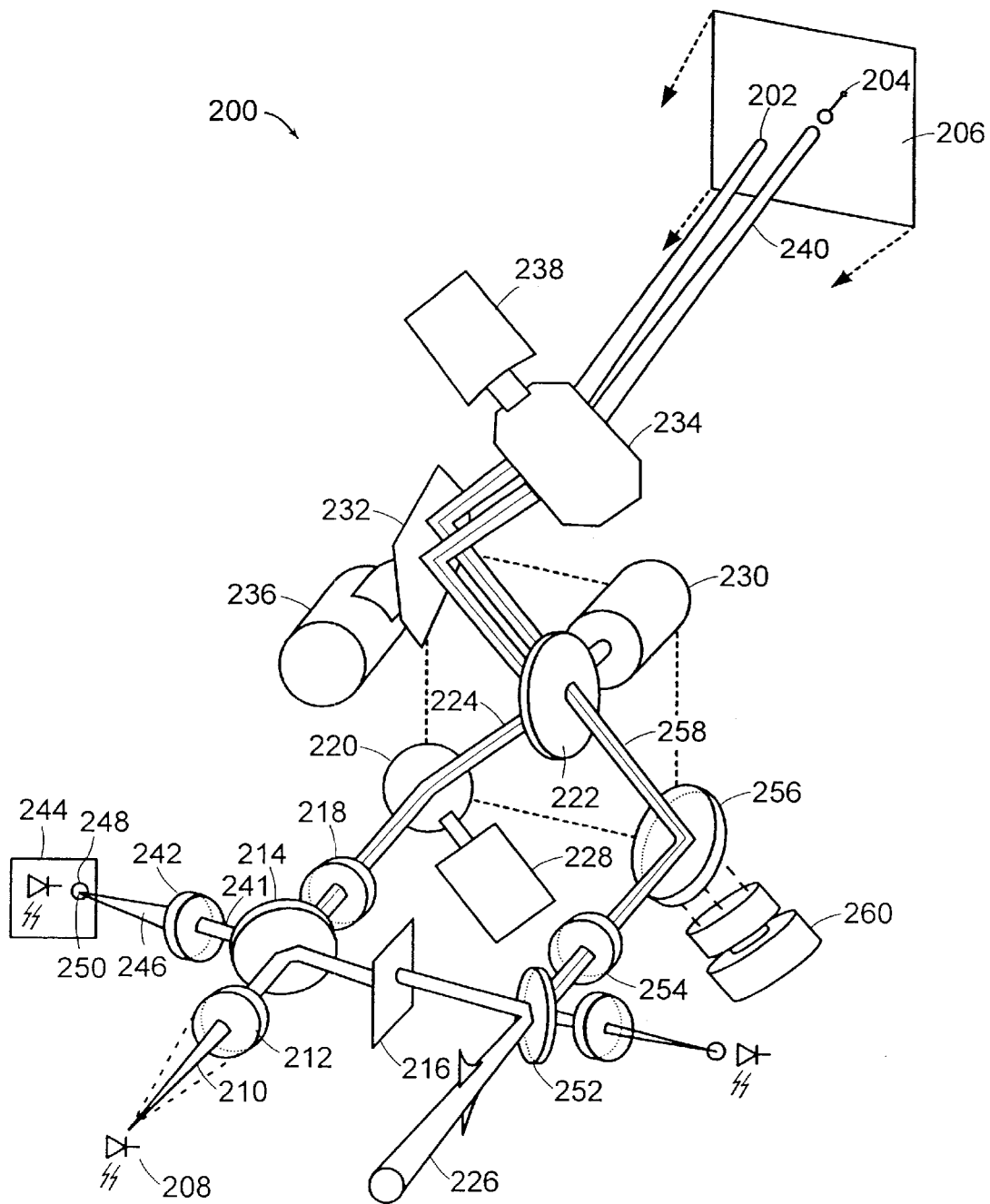
FIG. 3 is a schematic diagram of the optics for an eye tracking system which embodies the invention.

FIG. 3 is a schematic diagram of optics for an eye tracking system 200 which embodies the invention. The eye tracking system 200 tracks a target 202 associated with an eye (not shown) relative to a reference feature 204. The reflectivity of the reference feature 204 is different from the reflectivity of a background area 206.

The eye tracking system 200 includes a source of radiation 208 for generating an incident tracking beam 210. The incident tracking beam 210 may be collimated by a lens 212. A beamsplitter 214 may divert a portion of the incident tracking beam 210 to an absorbing stop 216. A second lens 218 may be used to focus the incident tracking beam emerging from the beamsplitter 214 onto the target 202.

A first pair of reflectors comprising a first 220 and a second reflector 222 is positioned in an optical path 224 of a tracking beam 210. The first pair of reflectors controls the position of the tracking beam 210. The second reflector 222 may be a beamsplitter 222 that reflects the tracking beam 210 in reflection and that passes a coagulating beam 226 in transmission. The beamsplitter 222 may be a dichronic beamsplitter that efficiently reflects at the tracking beam wavelength and that transmits without significant attenuation at the coagulating beam wavelength. Utilizing such a beamsplitter both reduces the optical path lengths of the tracking 210 and the coagulating beam 226, and reduces the number of optical components necessary to realize a practical system.

A first 228 and a second dither driver 230 are operatively connected to the first 220 and the second dither reflector 222, respectively. The first 228 and second dither driver 230 dithers the first reflector 220 in a first direction and the second reflector 222 in a second direction with an oscillatory motion having a dither frequency and a first and a second phase, respectively. The first and second phases may be orthogonal. The pair of dither drivers may be orthogonally mounted galvanometers operatively connected to the first pair of reflectors.

The required dither frequency depends upon several factors. For example, if the tracking beam is imaged on the retina of an eye at unit magnification, a two kilohertz dither frequency will correspond to approximately a 50 $\mu$m displacement per dither cycle at a target velocity of 10 cm/sec (greater than 300 degrees/sec in an eye). Such a dither frequency is sufficient to track a coagulating laser with a spot size of approximately 400 $\mu$m.

The eye tracking system 200 also includes a second pair of reflectors for positioning the tracking beam 210 onto the reference feature 204 and for positioning the coagulating beam 226 onto the target 202. The second pair of reflectors comprises a first 232 and a second tracking reflector 234. A pair of tracking drivers is operatively connected to the second pair of reflectors for controlling the position of the second pair of reflectors.

The pair of tracking drivers comprises a first 236 and a second tracking driver 238. The first 236 and second tracking driver 238 has a first and a second input (not shown) for accepting a first and a second direction control signal, respectively. The first and second direction control signals cause the pair of tracking drivers to move the second pair of reflectors in the first and the second direction, respectively. A tracking velocity of the pair of tracking drivers may be proportional to the product of a dither frequency of the pair of dither drivers and a spatial dimension of the reference feature 204.

The second pair of reflectors directs the tracking beam 210 to the target 202 where a reflected tracking beam 240 is directed back into the optical path 224. The reflected tracking beam 240 is consequently "de-scanned" through the first and second pair of reflectors. The lens 218 collects and collimates the reflected tracking beam 240. A portion of the reflected tracking beam 241 is reflected by the beamsplitter 214 to a focusing lens 242.

A reflectometer 244 is positioned in an optical path 246 of the reflected tracking beam 246 after the focusing lens 242. The reflectometer 244 may be a confocal reflectometer. The portion of the reflected tracking beam 241 is focused onto a confocal aperture 248. A diameter 250 of the confocal aperture 248 may be approximately the size of an image (not shown) of the reference feature 204. The reflectometer 244 provides an output signal with a phase corresponding to a phase of the reflected tracking beam 240.

The coagulating beam 226 is directed at a beamsplitter 252 which may divert a portion of the coagulating beam 226 to the absorbing stop 216. A lens 254 may be used to collimate the incident tracking beam emerging from the beamsplitter 252. A reflector 256 directs the coagulating beam 226 to the beamsplitter 222. The eye tracking system 200 may include a shutter (not shown) in an optical path 258 of the coagulating beam 226 for blanking the coagulating beam 226 so that a surgeon can control when the coagulating beam 226 is delivered to the target 202. The tracking system 100 may also include a camera 260 which views the optical path 258 to the target 202. An image received by the camera 260 is stabilized by the tracking system 200.

The eye tracking system 200 utilizes a signal processor (not shown) for comparing the phase of the reflectometer 244 output signal to the phases of the oscillatory motion in the first and second directions. The signal processor generates control signals which are coupled to the pair of tracking drivers 236, 238. The first and second direction control signals cause the coagulating beam to track relative to the reference feature.

Figure 4A:
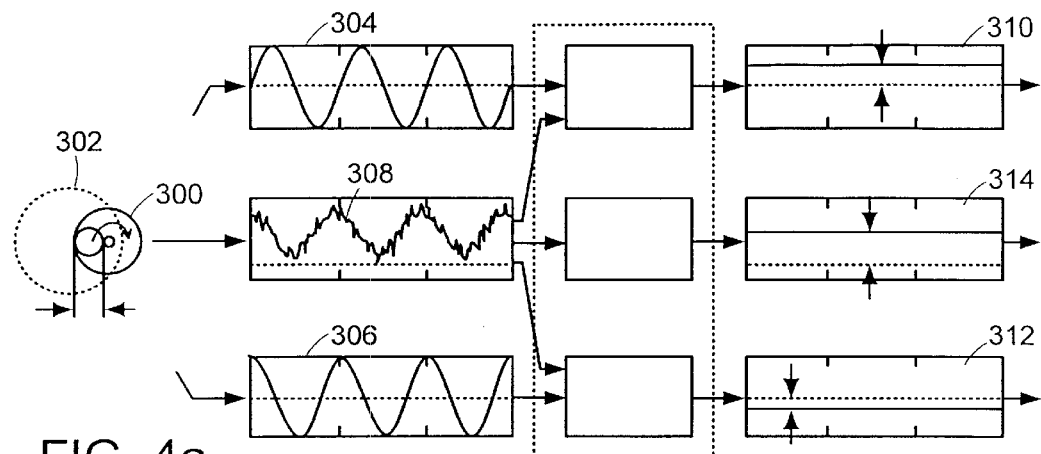
FIGS. 4A–C illustrates the operation of the signal processor.
Figure 4B:
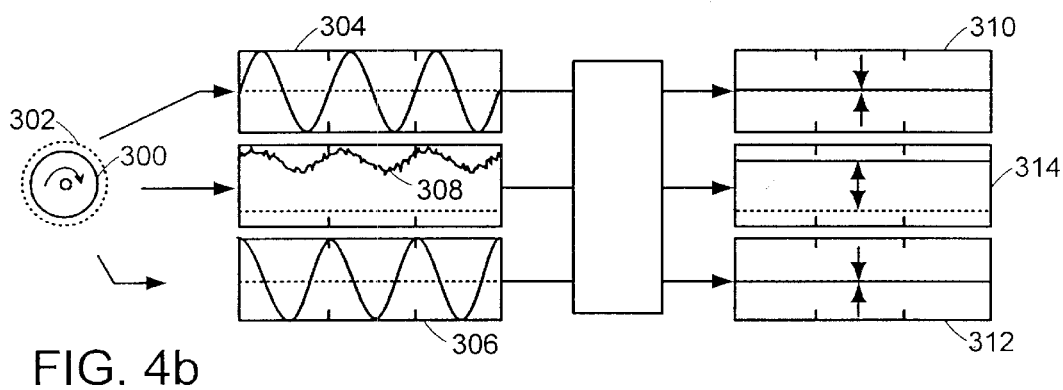
Figure 4C:
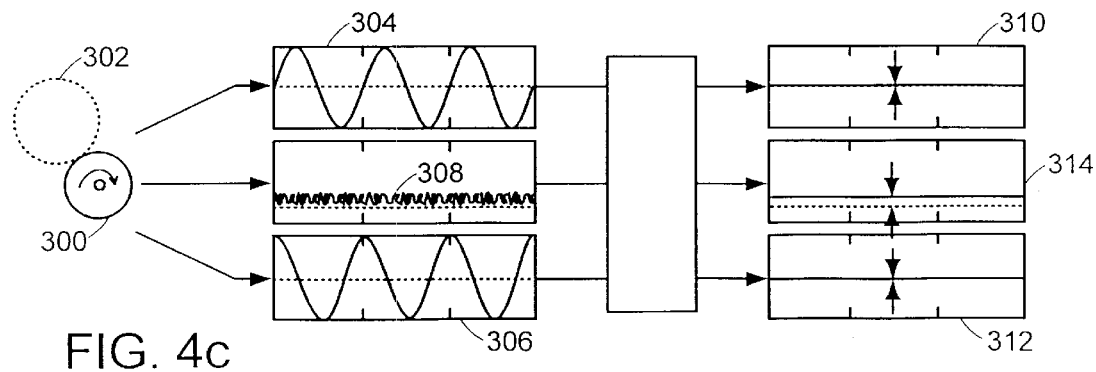

FIGS. 4A–C illustrates the operation of the signal processor. A dither circle 300 and an image of the reference feature 302 is schematically illustrated in three relative positions. Also, the oscillatory motion in the first 304 and second direction 306 with the first and the second phase, respectively, is illustrated. In addition, the output signal 308 of the reflectometer 36 (FIG. 1) is illustrated as a function of time. The corresponding first 310 and the second direction control signals 312 are also shown. Moreover, a tracking lock signal 314 is illustrated.

FIG. 4A illustrates the operation of the signal processor 42 (FIG. 1) when the dither circle 300 is partially within the image of the reference feature 302. The reflectometer produces a synchronous output signal 308 with a phase that depends on the direction in which the image of the reference feature 302 is displaced from the dither circle 300. The signal processor consequently generates a first and a second direction control signal proportional to an error in the first and the second direction. In addition, the signal processor generates a tracking lock signal 314 that indicates that the dither circle is locked onto the image of the reference feature 302.

FIG. 4B illustrates the operation of the signal processor when the dither circle 300 is centered and locked onto the image of the reference feature 302. The signal processor generates null first 310 and a second direction control signal 312. In addition, the signal processor generates a tracking lock signal 314 that indicates that the dither circle 300 is locked onto the image of the reference feature 302.

FIG. 4C illustrates the operation of the signal processor when the dither circle 300 is outside the image of the reference feature 302. The reflectometer output signal is low which indicates a loss of tracking. The signal processor generates a null first 310 and second direction control signal 312. In addition, the signal processor generates a null tracking lock signal 314 that indicates that the dither circle 300 is not locked onto the image of the reference feature 302.

Equivalents

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A tracking system comprising:
   a) a dithering device positioned in an optical path of a tracking beam for dithering the tracking beam in a first and a second direction with an oscillatory motion having a first and a second phase, respectively;
   b) a tracking device for controlling the position of a beam relative to a target and for controlling the position of the tracking beam relative to a reference feature, the tracking device including a first input for accepting a first direction control signal and a second input for accepting a second direction control signal, the first and second direction control signals causing the tracking device to move the beam in the first and the second direction, respectively;

c) a reflectometer positioned in an optical path of a reflected tracking beam, the reflectometer providing an output signal with a phase corresponding to a phase of the reflected tracking beam; and d) a signal processor for comparing the phase of the reflectometer output signal to the phases of the oscillatory motion in the first and second directions, the signal processor generating the first and the second direction control signals which are coupled to the first and second inputs of the tracking device, respectively, wherein the first and second direction control signals causing the beam to track relative to the reference feature.

2. The tracking system of claim 1 wherein the reference feature is in close proximity to the target.

3. The tracking system of claim 1 wherein the tracking device magnifies the beam.

4. The tracking system of claim 1 wherein the reflectometer is a confocal reflectometer.

5. The tracking system of claim 1 wherein the first and second phases of oscillatory motion are orthogonal.

6. The tracking system of claim 1 wherein the dithering device comprises a pair of orthogonally mounted galvanometers operatively connected to a reflector.

7. The tracking system of claim 1 wherein a tracking velocity of the tracking device is proportional to the product of a dither frequency of the dithering device and a spatial dimension of a reference feature.

8. The tracking system of claim 1 wherein the tracking beam is formed from a light emitting diode.

9. The tracking system of claim 1 wherein the reference feature comprises retro-reflecting material.

10. The tracking system of claim 1 further comprising a shutter for blanking the beam.

11. The tracking system of claim 1 further comprising an offset signal generator operatively coupled to the tracking device for displacing the beam with respect to the tracking beam a predetermined distance.

12. A method of tracking comprising:

a) directing a tracking beam to a reference feature;

b) dithering the tracking beam in a first and a second direction with an oscillatory motion having a first and a second phase, respectively;

c) positioning a reflector in an optical path of a beam;

d) measuring the phase of a reflected tracking beam reflected from the reference feature;

e) comparing the phase of the reflected tracking beam to the first and the second phase of the oscillatory motion; and f) repositioning the reflector a distance related to the comparison in step e), the distance causing the beam to track a displacement of the reference feature.

13. The method of claim 12 further comprising the step of positioning a reflector in an optical path of the tracking beam.

14. The method of claim 12 further comprising the step of displacing the beam relative to the tracking beam a predetermined distance.

* * * * *